United States Patent [19]

McCabe et al.

[11] Patent Number: 5,562,640
[45] Date of Patent: Oct. 8, 1996

[54] ENDOSCOPIC SURGICAL INSTRUMENT FOR ASPIRATION AND IRRIGATION

[75] Inventors: William J. McCabe, New Canaan; H. Jonathan Tovey, Milford; Paul A. Matula, Brookfield, all of Conn.

[73] Assignee: United States Surgical Corporation, Norwalk, Conn.

[21] Appl. No.: 333,881

[22] Filed: Nov. 3, 1994

Related U.S. Application Data

[63] Continuation of Ser. No. 781,062, Oct. 18, 1991, abandoned.

[51] Int. Cl.⁶ .................................................. A61M 1/00
[52] U.S. Cl. ................................ 604/280; 604/30; 604/43
[58] Field of Search ................................. 604/21, 22, 33, 604/245, 246, 247–249, 264, 280–284; 128/750

[56] References Cited

U.S. PATENT DOCUMENTS

| | | |
|---|---|---|
| Re. 31,272 | 6/1983 | Pevsner . |
| 1,740,174 | 12/1929 | Hervern ................................ 604/248 |
| 2,812,765 | 11/1957 | Tofflemire . |
| 3,208,145 | 1/1963 | Turner . |
| 3,527,203 | 9/1970 | Gravlee . |
| 3,735,751 | 5/1973 | Katz . |
| 3,850,175 | 11/1974 | Iglesias . |
| 3,929,126 | 12/1975 | Corsaut . |
| 3,994,297 | 11/1976 | Kopf . |
| 3,996,935 | 12/1976 | Banko . |
| 4,132,227 | 1/1979 | Ibe . |
| 4,149,315 | 4/1979 | Page, Jr. et al. . |
| 4,215,476 | 8/1980 | Armstrong . |
| 4,248,589 | 2/1981 | Lewis . |
| 4,320,761 | 3/1982 | Haddad . |
| 4,423,727 | 1/1984 | Widran et al. . |
| 4,465,470 | 8/1984 | Kelman . |
| 4,493,694 | 1/1985 | Wuchinich . |
| 4,517,962 | 5/1985 | Heckele . |
| 4,573,965 | 3/1986 | Russo ................................... 604/247 |
| 4,583,531 | 4/1986 | Mattchen . |
| 4,607,619 | 8/1986 | Seike et al. . |
| 4,643,711 | 2/1987 | Bates . |
| 4,655,743 | 4/1987 | Hyde . |
| 4,657,016 | 4/1987 | Garito et al. . |
| 4,717,380 | 1/1988 | Baumgartner . |
| 4,723,550 | 2/1988 | Bales et al. . |
| 4,726,374 | 2/1988 | Bales et al. . |
| 4,737,142 | 4/1988 | Heckele ................................ 604/280 |
| 4,744,360 | 5/1988 | Bath . |
| 4,747,820 | 5/1988 | Hornlein et al. . |
| 4,760,840 | 8/1988 | Fournier, Jr. et al. . |
| 4,769,018 | 9/1988 | Wilson ................................. 604/280 |
| 4,776,840 | 10/1988 | Freitas et al. . |
| 4,790,812 | 12/1988 | Hawkins, Jr. et al. . |
| 4,846,790 | 7/1989 | Hornlein et al. . |

(List continued on next page.)

FOREIGN PATENT DOCUMENTS

| | | |
|---|---|---|
| 0199848 | 11/1986 | European Pat. Off. . |
| 0327410 | 8/1989 | European Pat. Off. . |
| 0411170 | 2/1991 | European Pat. Off. . |
| 0463363 | 1/1992 | European Pat. Off. . |
| 0346712 | 12/1989 | France . |
| 587044 | 4/1977 | Germany . |
| 234608 | 4/1986 | Germany . |
| 2117245 | 10/1983 | United Kingdom . |
| WO8704610 | 8/1987 | WIPO . |
| WO9003152 | 4/1990 | WIPO . |

*Primary Examiner*—Manuel Mendez

[57] ABSTRACT

An endoscopic surgical instrument for aspiration and irrigation of a surgical site. The device includes at least one rotatable trumpet valve to provide for variable orientation of the device during use. Connection ports for irrigation fluid and a suction means are provided which communicate with a single lumen cannula which transports both the irrigation fluid and the suction pressure to the surgical site. The single lumen cannula is provided with a sleeve means to vary the pressure of the irrigation fluid to provide for high pressure application of the irrigation fluid to perform hydrodissection. A plurality of dissector tips and a novel means of securing the tips to the single lumen cannula are also disclosed.

32 Claims, 10 Drawing Sheets

U.S. PATENT DOCUMENTS

| | | |
|---|---|---|
| 4,881,523 | 11/1989 | Heckele . |
| 4,886,491 | 12/1989 | Parisi et al. . |
| 4,898,574 | 2/1990 | Uchiyama et al. . |
| 4,904,246 | 2/1990 | Atkinson . |
| 4,921,476 | 5/1990 | Wuchinich . |
| 4,921,477 | 5/1990 | Davis . |
| 4,922,902 | 5/1990 | Wuchinich et al. . |
| 4,924,851 | 5/1990 | Ognier et al. . |
| 4,931,047 | 6/1990 | Broadwin et al. . |
| 4,947,827 | 8/1990 | Opie et al. . |
| 4,959,058 | 9/1990 | Michelson ............... 604/280 |
| 4,968,306 | 11/1990 | Huss et al. ............... 604/264 |
| 5,053,002 | 10/1991 | Barlow ...................... 604/245 |
| 5,085,658 | 2/1992 | Meyer ........................ 606/46 |
| 5,100,377 | 3/1992 | Freitas et al. . |
| 5,125,910 | 6/1992 | Freitas . |
| 5,156,607 | 10/1992 | Kansas ...................... 606/107 |
| 5,186,714 | 2/1993 | Boudreault et al. ....... 604/33 |
| 5,188,591 | 2/1993 | Dorsey, III ................. 604/33 |
| 5,195,958 | 3/1993 | Phillips ...................... 604/21 |
| 5,197,948 | 3/1993 | Ghodsian . |
| 5,230,704 | 7/1993 | Moberg et al. . |
| 5,242,387 | 9/1993 | Loughlin ................... 604/33 |
| 5,244,459 | 9/1993 | Hill . |
| 5,247,966 | 9/1993 | Stevens et al. ............ 604/33 |
| 5,273,524 | 12/1993 | Fox et al. . |
| 5,303,735 | 4/1994 | Cerola et al. . |
| 5,306,237 | 4/1994 | Clement et al. . |
| 5,310,406 | 5/1994 | Sharpe et al. . |
| 5,312,327 | 5/1994 | Bales . |
| 5,312,332 | 5/1994 | Bales et al. . |
| 5,312,373 | 5/1994 | Freitas . |
| 5,322,503 | 6/1994 | Desai . |
| 5,324,254 | 6/1994 | Phillips . |
| 5,334,140 | 8/1994 | Phillips . |
| 5,348,555 | 9/1994 | Zinnanti . |

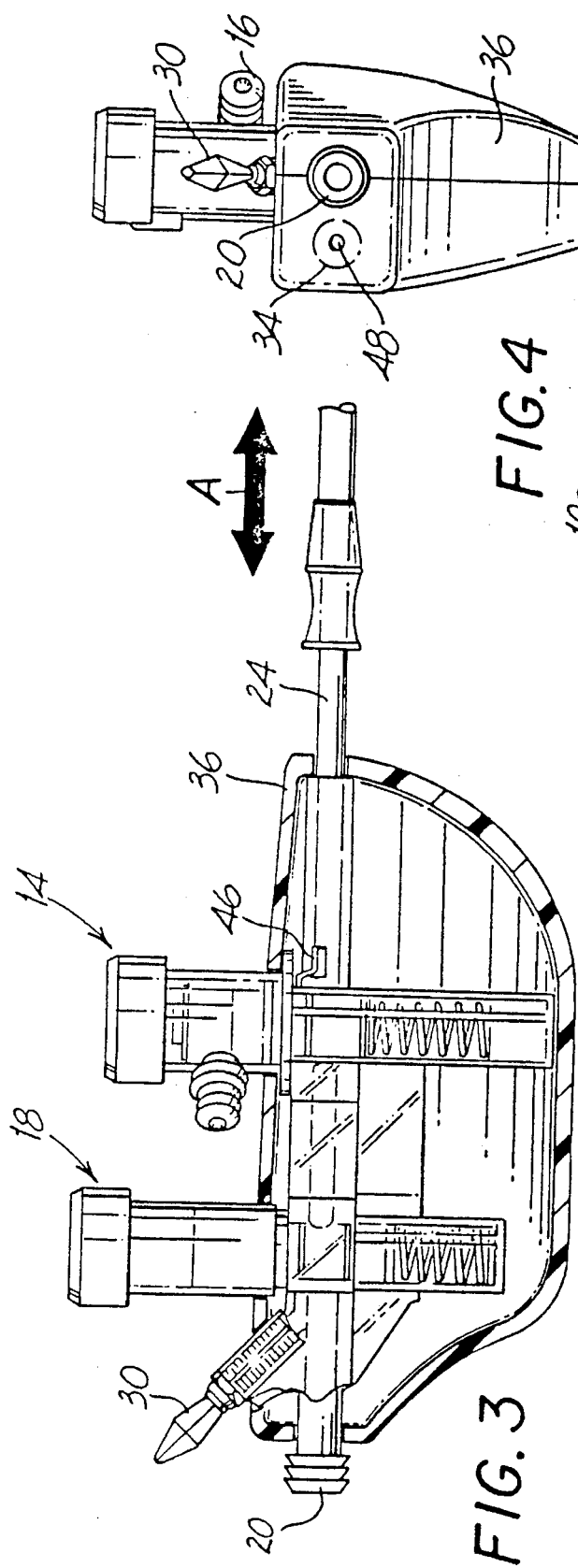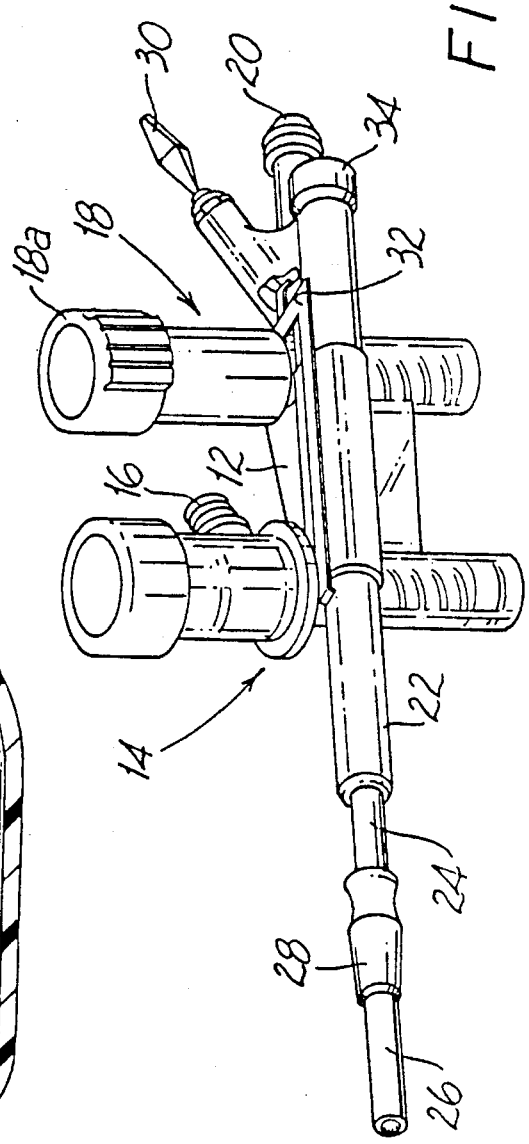

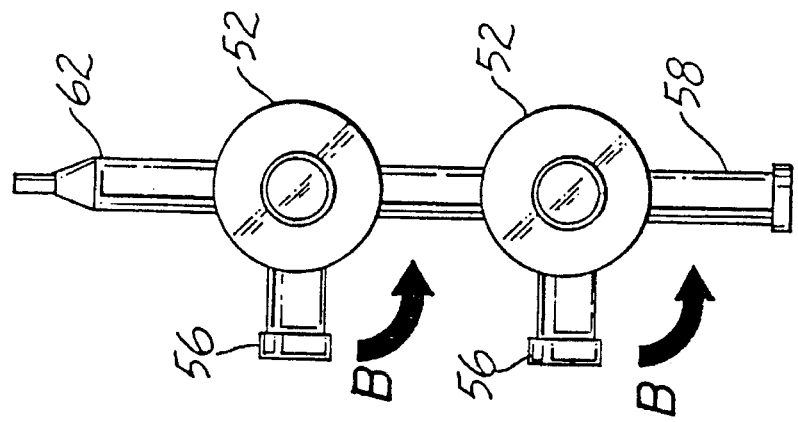
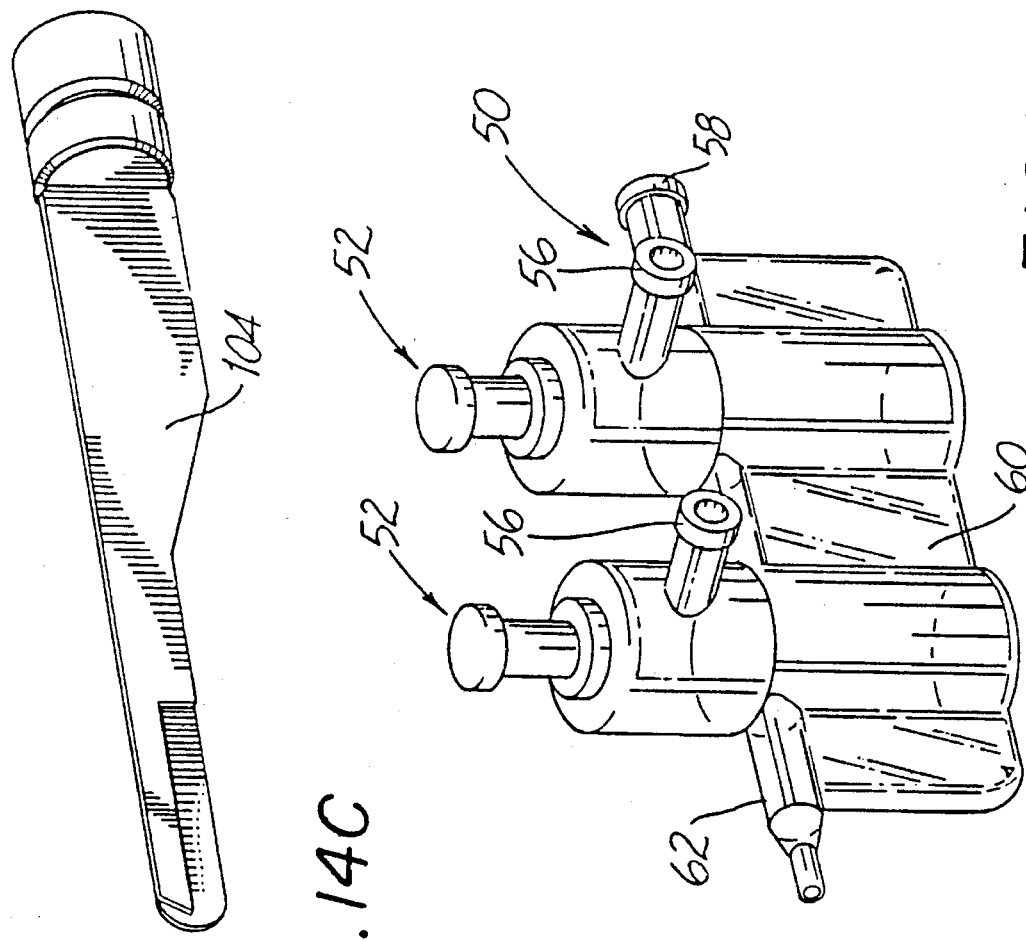

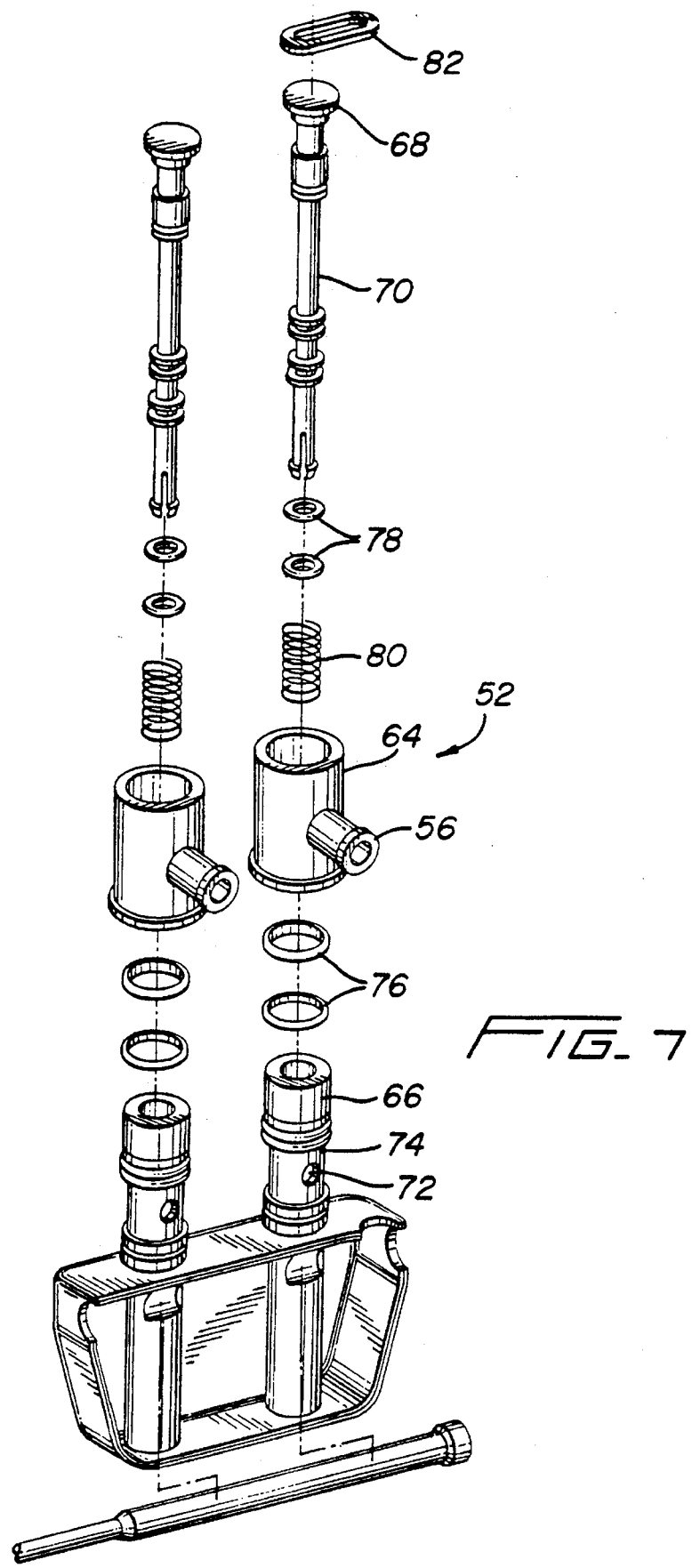

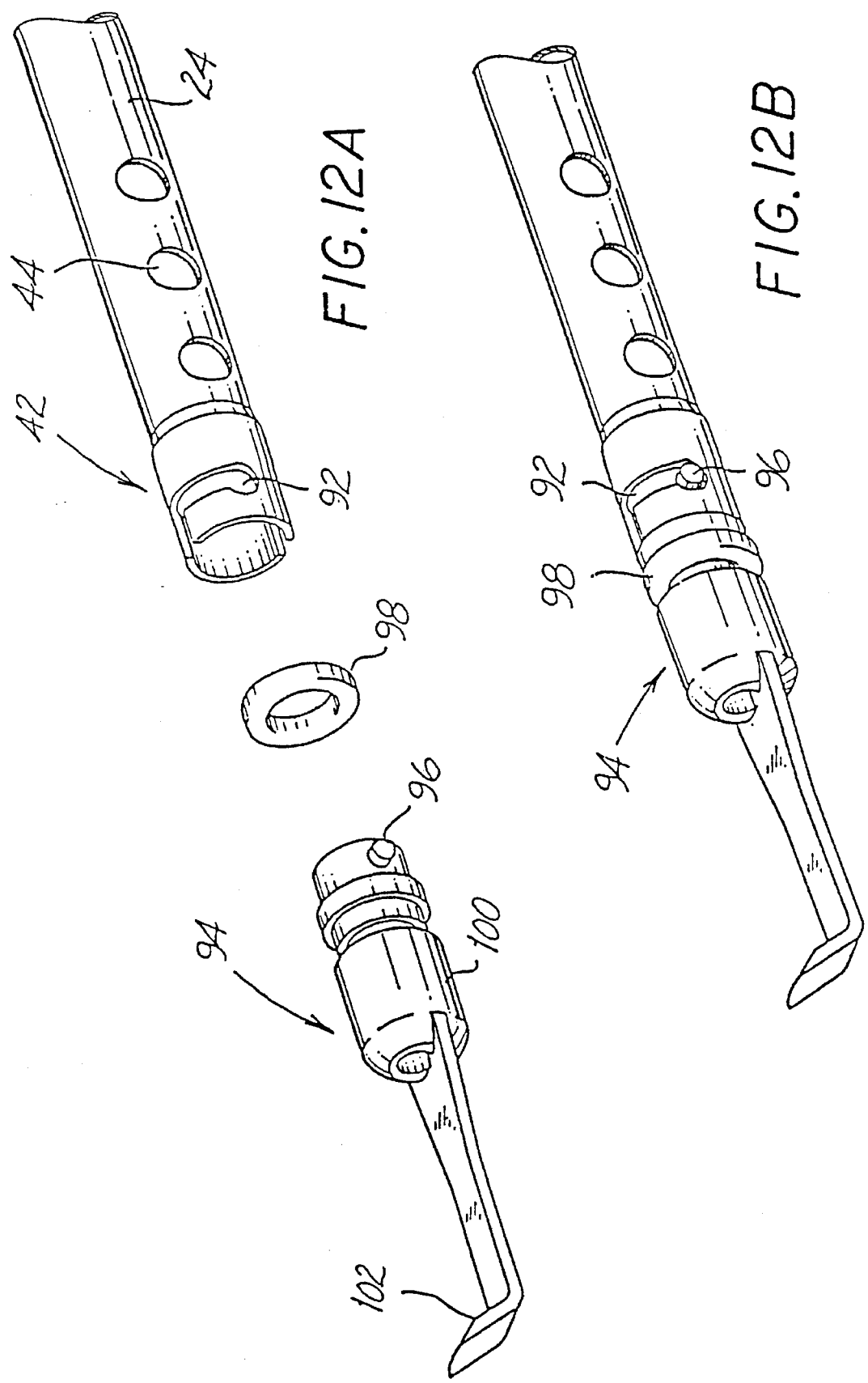

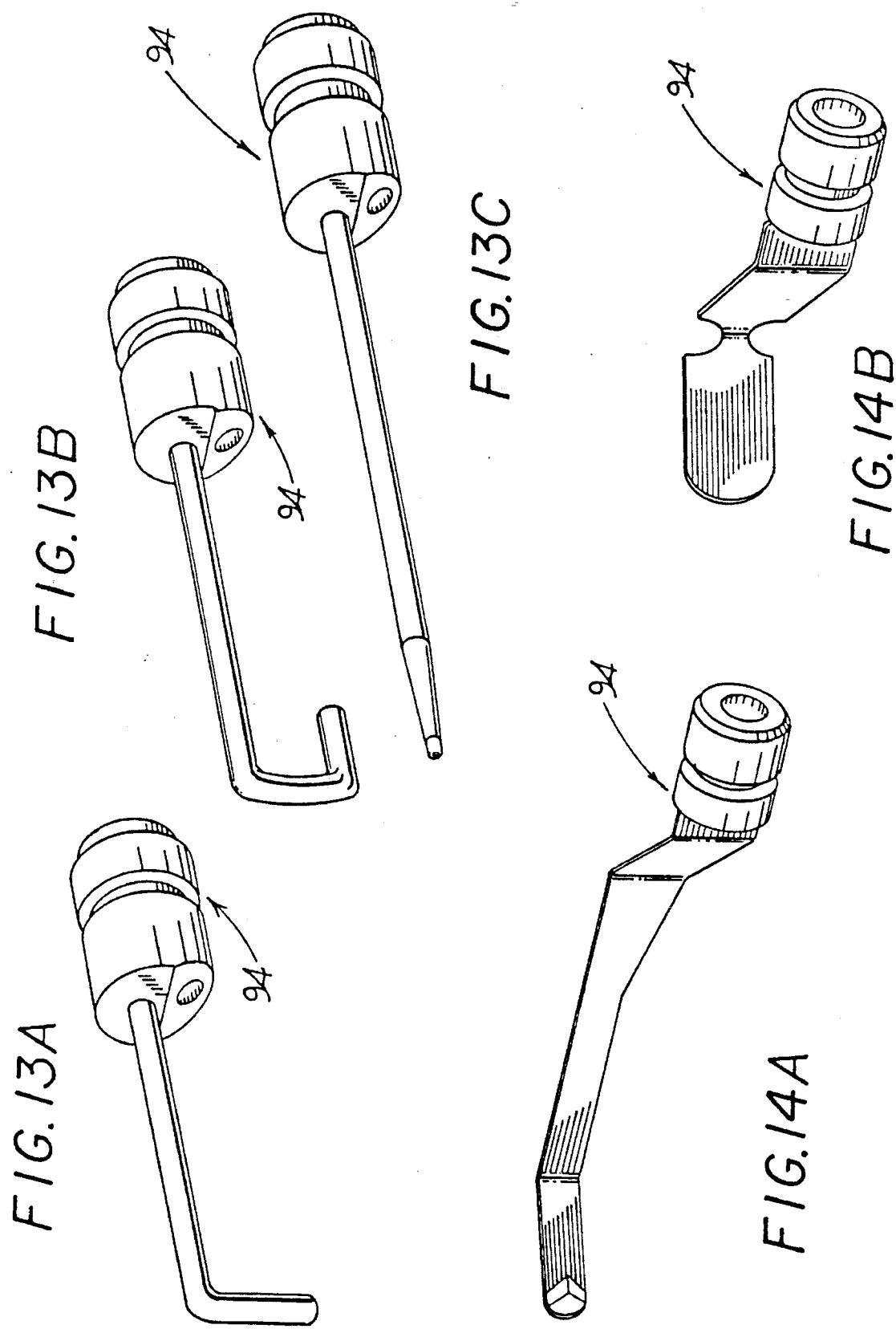

ENDOSCOPIC SURGICAL INSTRUMENT FOR ASPIRATION AND IRRIGATION

This is a continuation of application Ser. No. 07/781,062 filed on Oct. 18, 1991, now abandoned.

BACKGROUND OF THE INVENTION

1. Field of the Invention

The present invention relates to endoscopic surgical instruments, and more particularly to endoscopic surgical instruments for aspirating and irrigating a surgical site.

2. Discussion of the Prior Art

Surgical devices for providing irrigation fluid and suction to a surgical site to irrigate and evacuate the tissue in the area on which the surgical procedure is being performed are well known in the art. Several of these devices provide a handle member having switching means for turning on and off the flow of the fluid stream and the suction means, and typically connect the suction source and the fluid source to an elongated flexible tubular member which is positioned adjacent the surgical site. In many instances, the tube or catheter is comprised with a complex series of passages which provide a separate channel for the irrigation fluid and a separate channel for the suction means. Several devices provide a pump source to provide the fluid under pressure; however, other devices provide a source of irrigation fluid which is operable under head pressure to gently wash the tissue. The prior art devices typically provide a large tube or catheter which enclose the several channels to deliver the fluid and provide the suction during oral surgery, or invasive surgery which allows for the positioning of the cumbersome tubing.

Several of the prior art devices provide numerous features including electrocautery, laser dissection, and viewing capabilities. Typically, the handle grip includes on/off switches in the form of trumpet valves which allow the surgeon to selectively choose the suction or irrigation feature. Many devices provide a pistol-type hand grip which allows the surgeon to operate the device with the thumb-actuated valves. Other devices provide tubular connections such as Luer-type connectors to couple the irrigation source or the suction source to the catheter or tube.

With the recent developments in endoscopic and laparoscopic surgical procedures, it is necessary to provide a device in which many of the functions provided by the more complex and cumbersome prior art devices are included in a streamlined construction in which many of the features are provided in a single unit. In laparoscopic and endoscopic surgical procedures, a small incision or puncture is made in the patient's body to provide access for a tube or cannula device. The cannula is inserted into the patient's body through the provision of a trocar assembly which further includes an obturator for penetrating the body wall. After the obturator is removed, the cannula remains in place to maintain access to the surgical site. Once the cannula is in place, the surgical instrument may be inserted through the cannula to perform the procedure, while the surgical area is viewed through an endoscope or a miniature camera inserted through secondary cannulas to display the procedure on a video monitor.

The prior art devices are subject to several disadvantages when considered for use in laparoscopic or endoscopic surgical procedures. The primary focus behind such surgical procedures is that the surgery is minimally invasive to the patient's body, consequently reducing damage to surrounding tissue and organs and reducing the scarring resulting from the operation, which, as a result, greatly reduces recovery time for the patient. The prior art devices, which typically provide a plurality of channels in the tube or catheter portion to transport the suction and irrigation means to the surgical site, are generally provided for invasive type surgery which allows the larger diameter catheters to be manually positioned adjacent the surgical objective through large incisions.

A further limitation to which the prior art devices are subjected involves positioning of the device during the surgical procedure. Many of these devices are provided with a pistol-type grip which requires a particular orientation of the device in relation to the surgeon's position during the procedure. Should it become necessary for the device to be relocated during the surgical procedure, it is often times uncomfortable to the surgeon to position the device at an angle that does not facilitate operation of the valve members to turn the various features on and off. As a result, the effectiveness of the device is limited, and in many times requires a surgical assistant to operate the device for the surgeon.

Typical suction and irrigation devices having a hand grip in the shape of a pistol are disclosed in U.S. Pat. No. 4,149,315 to Page, Jr. et at. and U.S. Pat. No. 4,776,840 to Freitas et at. Page, Jr. et at. provides a dental suction/irrigation device which includes an elongated tube member which transports the suction means and the irrigation means to the tissue site. The elongated tubular member comprises a pair of concentric tubes where the inner tube provides the irrigation fluid and the outer tube is provided for the suction. A pair of trumpet valves are provided to actuate the irrigation source and the aspiration source. Freitas et at. discloses a similar device but includes a complex internal manual pump to provide the irrigation fluid. A second flexible tube is provided for a vacuum source to evacuate fluid and gases from the surgical site.

U.S. Pat. No. 4,744,360 Bath provides a surgical device for removing cataract lenses which includes an optical fiber for laser surgery which is surrounded by an irrigation sleeve and a separate aspirator sleeve which provides fluid for irrigation and suction for evacuation, respectively, of the surgical site.

A Cabot Medical Corporation brochure (copyright 1990) discloses a suction/irrigation probe which includes a hydrodissection insert which comprises a rod which passes through the tube of the suction/irrigation probe to adjust the flow of the irrigation fluid.

Other known devices include U.S. Pat. No. 4,921,476 and U.S. Pat. No. 4,493,694 to Wuchinich, and U.S. Pat. No. 3,527,203 to Gravlee, which include a tube having several channels for carrying the irrigation fluid separately from the suction device.

The novel endoscopic surgical device for suction and irrigation of tissue during a surgical procedure obviates the disadvantages encountered in the prior art and provides a compact instrument which includes many of the features necessary to perform the surgical procedure, and which is dimensioned to fit through a cannula for the performance of endoscopic or laparoscopic surgical procedures. The device of the present invention allows a surgeon to operate the suction and irrigation device with either hand and at any orientation to the surgical site comfortably and without assistance.

SUMMARY OF THE INVENTION

The present invention provides a novel irrigation and aspiration device for performing endoscopic or laparoscopic surgical procedures which allows the surgeon to operate the device with either hand and at any orientation to the patient's body. The device includes numerous features necessary for the performance of a surgical procedure such as dissection of tissue, or to provide suction and irrigation to a surgical site where the procedure is performed with additional instruments.

The suction and irrigation device of the present invention comprises a vailably orientable subassembly which may be incorporated into various outer enclosures or housings dependent on the surgeon's preference and on the type of surgical procedure in which the surgical instrument is to be used. The subassembly essentially comprises a connection port for a source of suction and means to actuate the source of suction through the port, as well as a connection point for irrigation fluid with means to actuate the irrigation source through the port. A single lumen cannula is provided which communicates with the actuating means for both the suction port and the irrigation port which transports the suction means and the irrigation fluid to the surgical site. The device may further include a port for an optical fiber for the performance of laser surgery which further communicates with the single lumen cannula to locate the optical fiber through the cannula to the surgical site. Furthermore, electrocautery means may be provided for the performance of cauterization procedures at the surgical site.

The single lumen cannula is provided with a connection means at its distal end for the interchangeable connection of various operative tips which allows the surgeon to perform various surgical procedures. These tips include a surgical knife, blunt dissectors, and a nozzle for high pressure hydrodissection. The cannula is provided with a plurality of apertures at the distal end for communicating the interior of the cannula with the surrounding environment at the surgical site.

A further feature of the device is the hydrodissection capability, in which the high pressure fluid may be directed to the tissue at high pressure to dissect the tissue. In this regard, a concentric outer sleeve member is provided along the length of the cannula which is longitudinally slidable to cover one or all of the apertures at the distal end of the cannula. This allows the surgeon to vary the pressure and provides a visual indication for adjusting the pressure at the distal end.

A further feature of the present invention is the vailably orientable valve members which allows the surgeon to operate the device with either hand and at any orientation in relation to the patient's body. Preferably, the optical fiber connection port is axially aligned with the longitudinal axis of the single lumen cannula. At least one of the connection ports for either the aspiration means or the suction means, or both, includes a rotatable trumpet valve to allow the surgeon to rotate the valve at least 180° from one position perpendicular to the longitudinal axis of the single lumen cannula to a second position perpendicular to the longitudinal axis of the single lumen cannula on the opposite side of the cannula. If one connection port is rotatable, the other may be rotatable, or may extend from the distal end of the device so that the connection port is within substantial parallel alignment with the longitudinal axis of the single lumen cannula and the laser optical fiber connection port. Furthermore, the connection for the electrocautery feature preferably includes a bayonet-type male connector which extends at an angle to, but generally in the same direction as, the longitudinal axis of the single lumen cannula. These features allow the surgeon to vary the orientation of the device and operate the device with either hand by rotating the trumpet valves so that the tubes or hoses which deliver the suction means or the irrigation fluid are in an unobstructed position.

BRIEF DESCRIPTION OF THE DRAWINGS

The foregoing features of the present invention will become more readily apparent and may be understood by referring to the following detailed description of the endoscopic surgical aspiration and irrigation instrument, taken in conjunction with the accompanying drawings, in which:

FIG. 1 illustrates a perspective view of the subassembly of the endoscopic surgical instrument for aspiration and irrigation according to the present invention;

FIG. 3 illustrates a side plan view in partial cross section of the embodiment of FIG. 2;

FIG. 4 illustrates a rear plan view of the device of FIG. 2;

FIG. 5 illustrates a perspective view of a second embodiment of the subassembly of the endoscopic surgical instrument for aspiration and irrigation according to the present invention;

FIG. 6 illustrates a top plan view of the device of FIG. 5;

FIG. 7 illustrates an exploded perspective view of the valve mechanism of the device of FIG. 5;

FIGS. 12a and 12b illustrate an exploded perspective view and a perspective view, respectively, of the distal end of the single lumen cannula having a dissector tool mechanism attached thereto;

FIGS. 13a through 13c illustrate various electrocautery dissectors for use with the device of the present invention;

FIGS. 14a through 14c illustrate various blunt dissectors and surgical knives for use with the device of the present invention;

DETAILED DESCRIPTION OF THE PREFERRED EMBODIMENTS

Figure 2:
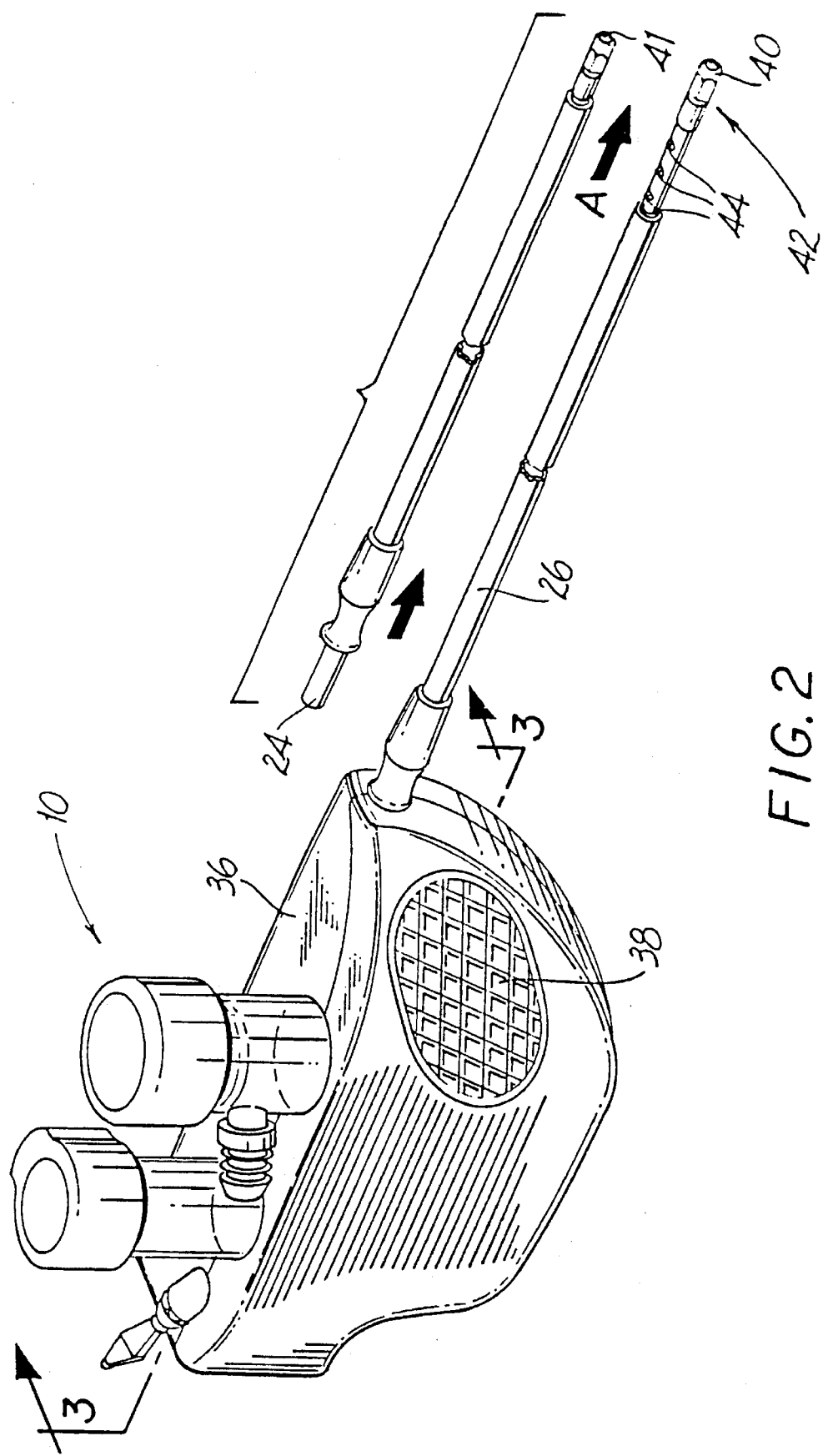
FIG. 2 illustrates a perspective view of the present invention including an external housing according to a first embodiment.

Referring now in specific detail to the drawings, in which like reference numerals identify similar or identical elements throughout the several views, FIG. 1 shows the endoscopic surgical instrument for aspiration and irrigation according to the present invention. Instrument 10 comprises a body portion 12 to which at least a pair of valve members 14 and 18 are attached. Preferably, at least one valve member, namely valve member 14, includes a rotatable connection port 16 for coupling a source of irrigation or a source of suction thereto. The function of rotatable connection port 16 will be discussed below. Valve member 18 may include a rotatable connection port; however, in a preferred embodiment valve member 18 includes a rotatably lockable actuator 18a for maintaining a source of constant irrigation or suction. Connection port 20 is controlled by valve member 18.

Body portion 12 essentially comprises a mixing chamber which communicates with both connection port 16 and connection port 20 through valve member 14 and 18, respectively. Body portion 12 extends into coupling member 22 which couples the mixing chamber within body portion 12 with a single lumen cannula 24. Single lumen cannula 24 provides a means for transporting the irrigation fluid or the suction force from their respective sources to the surgical site. Single lumen cannula 24 simplifies the construction of device 10 and significantly reduces cost in that a single tubular member having a reduced diameter single channel therethrough is utilized to carry both the suction and irrigation fluid to the surgical site.

Preferably, single lumen cannula 24 is enclosed within outer sleeve member 26 which concentrically surrounds and contacts single lumen cannula 24 along its length and is slidable in a longitudinal direction by grip member 28. The purpose of the slidable outer sleeve will be discussed below.

Device 10 may further include a bayonet-type connector 30 for providing electrocautery capabilities to device 10. Bayonet connector 30 is in electrical contact with single lumen cannula 24 through the provision of bus bar 32. Bayonet connector 30 provides for cauterization at the surgical site and for electrodissection of tissue. Device 10 may further include laser dissection means, which may be provided by an optical fiber through optical fiber port 34.

FIG. 2 illustrates the device of FIG. 1 enclosed in a working housing 36 which provides for gripping and handling of device 10. Housing 36 may be provided with scored portion 38 in one or several locations to facilitate gripping. As is seen in FIG. 2, single lumen cannula 24 is enclosed by outer sleeve member 26 which is slidable between a proximal position whereby apertures 44 are exposed at the distal end 42, to a distal position where outer sleeve 26 covers apertures 44. A hydrodissection tip 40 is shown as connected to the distal end 42 of single lumen cannula 24. In use, device 10 may be utilized for hydrodissection purposes. In such a case, a high pressure irrigation fluid source is utilized and connected, preferably to either of connection port 16 or connection port 20. As the irrigation fluid exits the aperture 41 at the end of hydrodissection tip 40, the pressure at which the fluid exits may be regulated and varied by sliding outer sleeve 26 in the direction of arrow A to cover one or more of apertures 44. Covering apertures 44 will increase the pressure of the fluid exiting tip 40 to provide for greater or less pressure of the irrigation and dissection fluid.

Preferably, outer sleeve 26 is constructed of an electrical insulating material, such as plastic, or may be provided with an electrically insulating shrink tubing, so that when device 10 is used for electrocautery purposes, the risk of shock is mitigated. FIG. 3 shows the electrical connection of bayonet connector 30 with single lumen cannula 24 at connection point 46.

FIG. 4 illustrates a rear view of the device of FIG. 2 which illustrates connection port 20 as being in axial alignment with valve members 14 and 18, while optical fiber port 34 is in direct axial alignment with single lumen cannula 24. Optical fiber port 34 is provided with a sealing means 48 which generally comprises a rubber type gasket which is penetrable by the optical fiber and seals around the fiber to prevent loss of suction pressure and leakage of irrigation fluid.

FIGS. 5 and 6 illustrate an alternate embodiment 50 of the instrument of FIG. 1. Instrument 50 comprises a pair of rotatable trumpet valve members 52 which are secured to a body portion 60 and are positioned directly in line with a coupling member 62 which extends into the single lumen cannula described above. An optical fiber port 58 is provided which is directly in line with coupling member 62. Rotatable trumpet valve members 52 include rotatable connection ports 56 whose function will be discussed below.

Turning to FIG. 7, there is shown the rotatable trumpet valve members 52 (as well as valve member 14 discussed above in connection with Figure 1). Valve members 52 essentially comprise a rotatable outer housing 64 to which connection port 56 is coupled. Outer housing 64 fits over inner housing 66, and valve stem 70 of actuator knob 68 extends through the inner and outer housings. Inner housing 66, is provided with an opening 72 which communicates a chamber as defined by the inner wall of outer housing 64 and chamber wall 74 to allow for the passage of fluid or suction pressure upon actuation of valve member 52. A pair of gaskets 76 are provided which seal the top and bottom of the chamber between the outer housing 64 and the inner housing 66, to prevent leakage while maintaining the rotatable feature. A second pair of gaskets 78 are secured to stem 70 for actuation of valve member 52. A spring means 80 is provided, as is common in trumpet-type valves. In addition, a locking ring 82 may be provided to maintain the valve in the continuously on position. The locking ring may be eliminated such as shown in FIG. 1, where a camming surface is provided on the interior surface of actuator knob 18a which engages a cam surface on the outside of outer housing 64.

Figure 8:
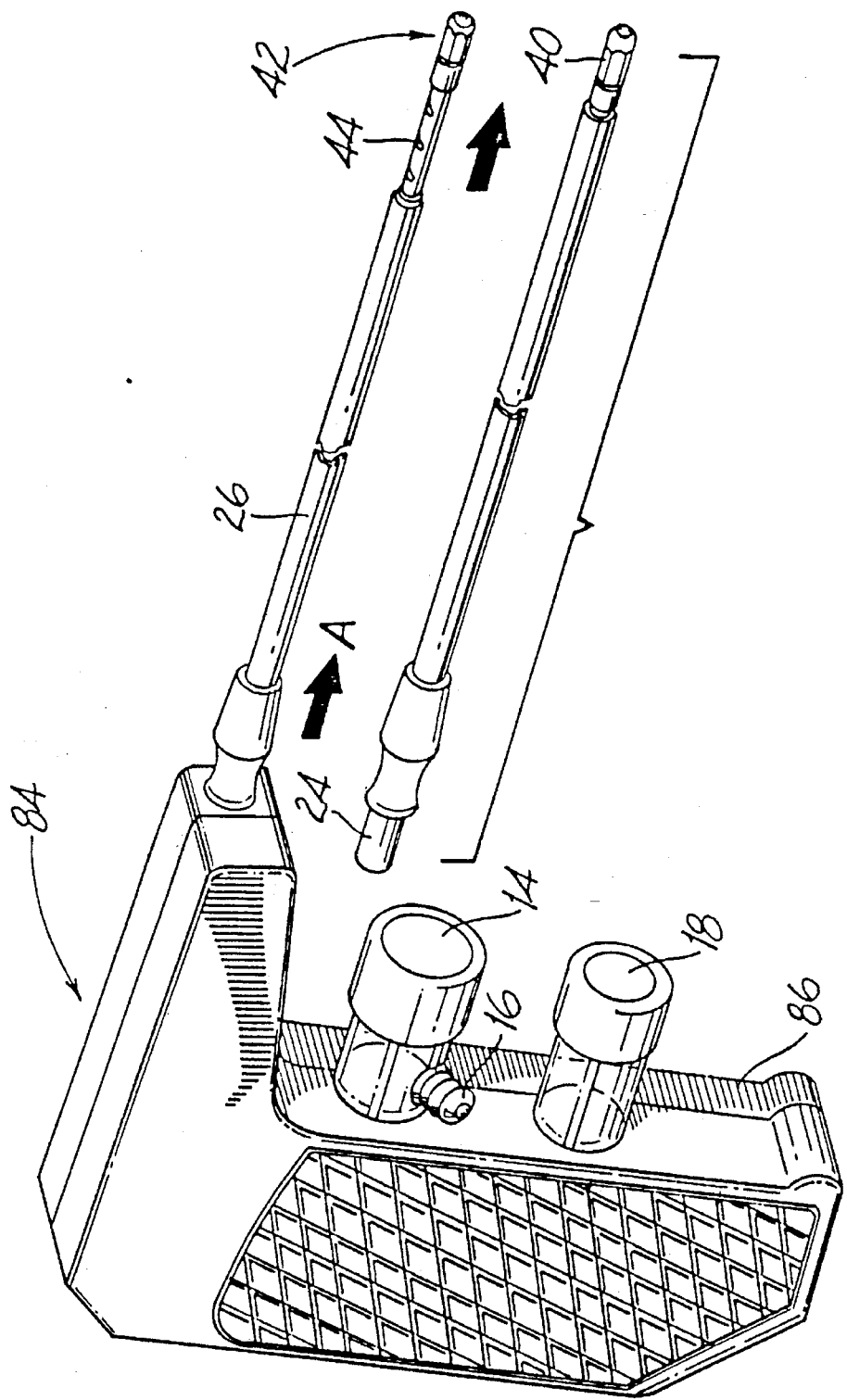
FIG. 8 illustrates a perspective view of a second embodiment of the outer enclosure employing the device of FIG. 1 according to the present invention.
Figure 10:
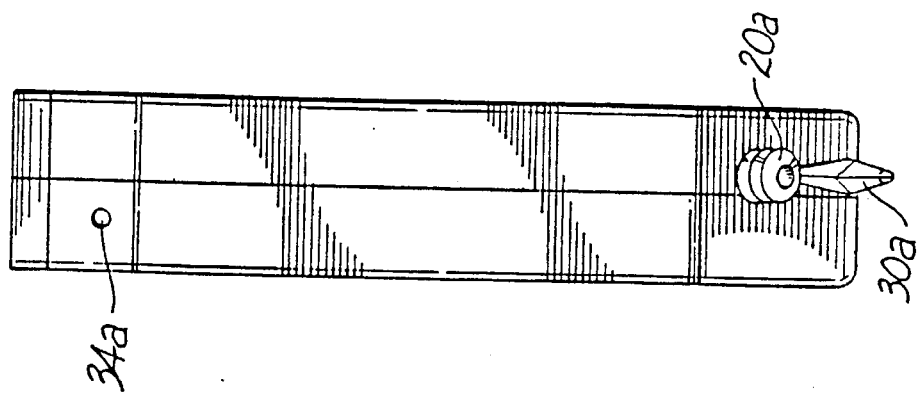
FIG. 10 illustrates a rear plan view of the device of FIG. 8.

Turning now to FIG. 8, there is illustrated a further embodiment of the surgical instrument for aspiration and irrigation according to the present invention, in which a pistol-type housing 86 is provided. Housing 86 encloses device 10a and includes valve members 14 and 18, where valve member 14 includes rotatable connection port 16. Extending from housing 86 is single lumen cannula 24 which includes an outer sleeve member 26 longitudinally slidable in the direction of arrow A in the manner described above. FIG. 10 illustrates a rear view of the device of FIG. 8 which shows the optical fiber connection port 34a as well as connection port 20a and bayonet connector 30a.

Figure 9:
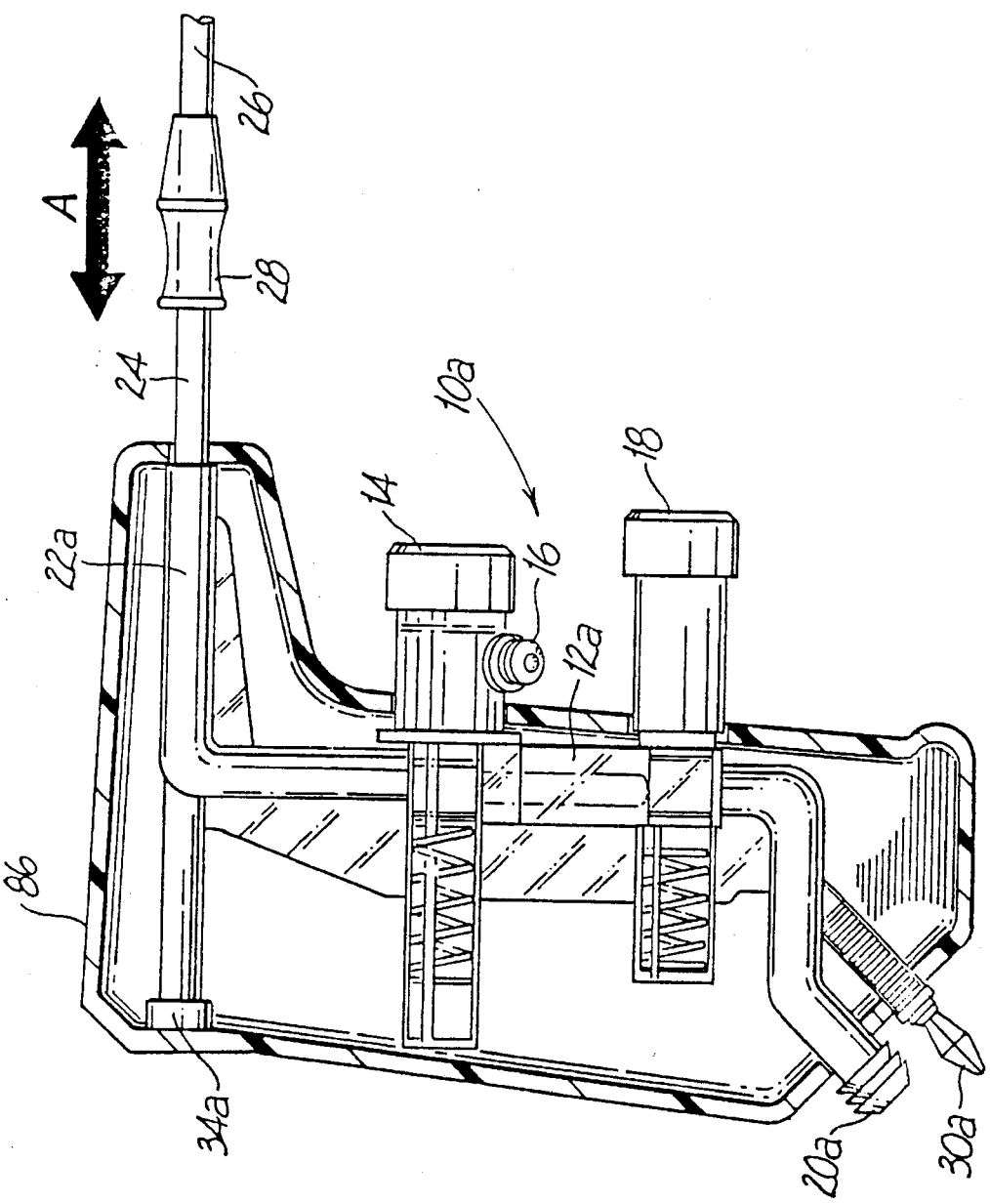
FIG. 9 illustrates a side plan view in partial cross section of the device of FIG. 8.

FIG. 9 illustrates surgical instrument 10a enclosed in housing 86. Connection port 20a extends in a rearward direction from body portion 12a and exits the device as shown. Coupling member 22a is provided as shown which engages body portion 12a and single lumen cannula 24, and further includes means to connect optical fiber port 34a in direct axial communication with single lumen cannula 24. Outer sleeve member 26 is slidable in a longitudinal direction in the direction of arrow A through the provision of grip member 28.

Figure 11:
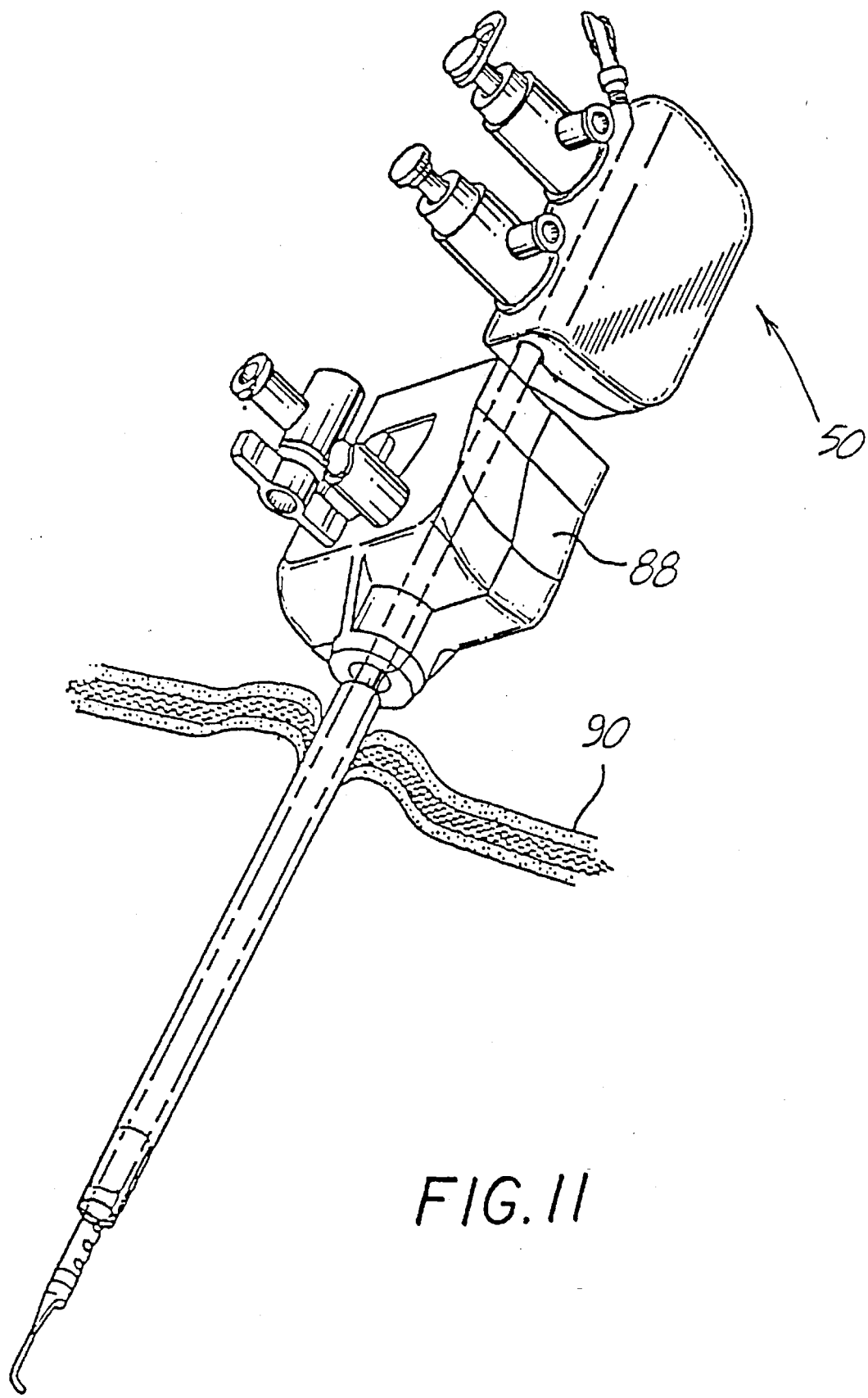
FIG. 11 illustrates a perspective view of the endoscopic surgical instrument for aspiration and irrigation according to the present invention in use during a surgical procedure.

FIG. 11 illustrates the suction and irrigation device 50 according to the present invention in use at a surgical site. The body wall 90 of the patient is penetrated by a trocar assembly, the cannula 88 of which remains in place after the pointed obturator has been removed. Instrument 50 is inserted to the surgical site through cannula 88 as shown to perform the surgical procedure.

FIGS. 12a and 12b illustrate a novel means for connecting the working tip of the device of the present invention to the single lumen cannula. The tips may be interchangeable and may include a plurality of tips such as that shown in FIGS. 12a and 12b, as well as FIGS. 13a through 13c and FIGS. 14a through 14c. As shown in FIGS. 12a and 12b, key slots 92 are provided at the distal end 42 of single lumen cannula 24 for accepting the key posts 96 of dissector tip 94. Tip 94 is secured through a sealing gasket 98 to key slots 92. Dissector tip 94 includes a central passageway 100 to maintain fluid communication with the interior of single lumen cannula 24 adjacent the working tip 102. Tip 102 may further include a knife 104 as shown in FIG. 14c.

Figure 15A:
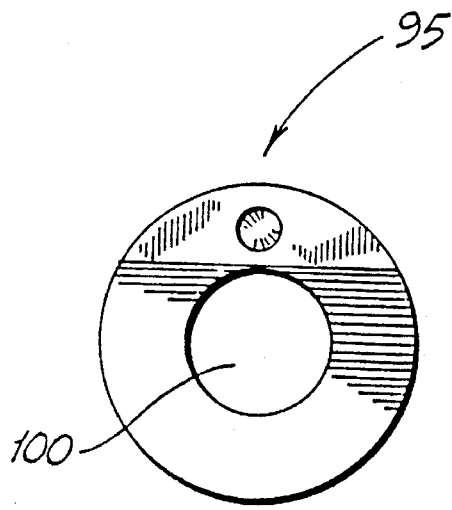
FIGS. 15a and 15b illustrate a coupling member for use with the dissectors of FIGS. 13a through 13c.
Figure 15B:
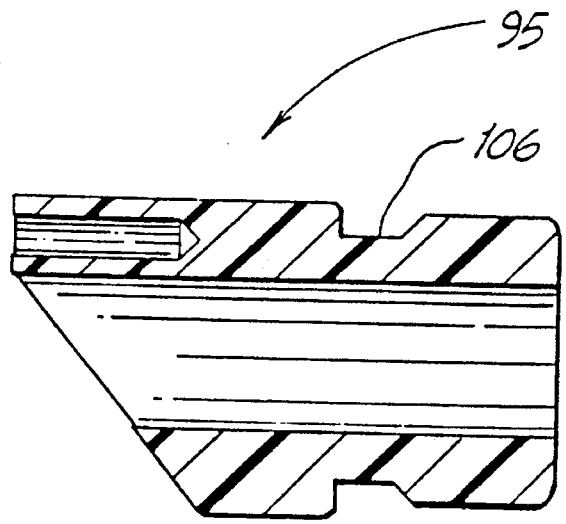
Figure 16A:
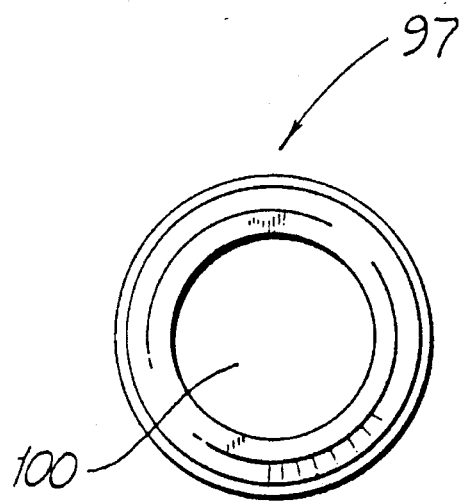
FIGS. 16a and 16b illustrate a coupling member for use with the dissectors of FIGS. 14a through 14c.
Figure 16B:
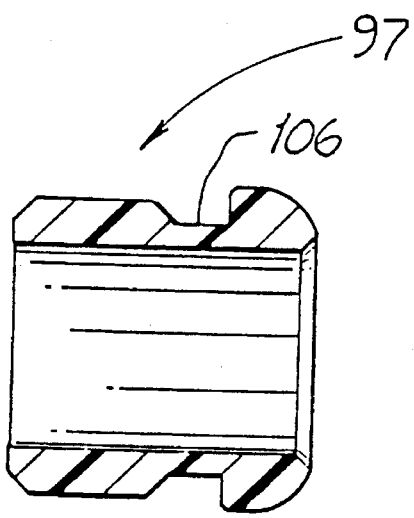

An alternate means of securing detachable dissector tip 94 to distal end 42 of single lumen cannula 24 may be accomplished through the provision of coupling members 95 and 97 as shown in FIGS. 15 and 16. In this embodiment, an annular groove 106 is provided which engages a detent on the interior of distal end 42 to snap fit coupling members 95 and 97 therein. In addition, a threaded connection may be used.

In use, the instrument of the present invention provides a variably orientable aspiration and irrigation device which may also be used for dissecting tissue. The instrument is constructed to accommodate use with either hand and at any orientation to the patient's body during the surgical procedure through the provision of rotatable valve members which are at least 180° rotatable so that the connection hoses to the irrigation and aspiration sources may be oriented on either side of the device. Furthermore, the connection ports for at least an optical fiber for laser surgery purposes as well as a bayonet connection member for electro-cautery procedures are provided substantially parallel to the longitudinal axis of the single lumen cannula which communicates the instrument with the surgical site. In addition, one of the rotatable valve members may be replaced by a locking valve member and the connection port thereto extends directly from the distal end of the device in parallel with the longitudinal axis of the single lumen cannula.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical device for aspiration and irrigation of a surgical site, comprising:
    a handle means including
        a mixing chamber positioned within said handle means,
        first connection means for a source of irrigation fluid,
        means for actuating said first connection means,
        second connection means for an aspirating source,
        means for actuating said second connection means, and
        an access means in communication with said mixing chamber for accommodating a surgical tool; and
    an endoscopic portion extending from said handle means including
        a single lumen cannula means having a proximal end extending from said handle means, said cannula means adapted to communicate with said aspirating source and said fluid source through said first and second connection means at said proximal end of said cannula means, said cannula means communicating with said access means through said mixing chamber, a distal end of said cannula means being positionable adjacent a surgical site to selectively transport said fluid and an aspirating force to said distal end, wherein said first and second connection means and said cannula means communicate with said mixing chamber for delivery of said fluid and said aspirating force to said distal end of cannula means.

2. A surgical device according to claim 1, wherein said actuating means comprise trumpet valve means, said trumpet valve means including said connection means.

3. A surgical device according to claim 2, wherein said trumpet valve means include rotatable connection means rotatable about a central axis of said trumpet valve.

4. A surgical device according to claim 1, further comprising connection means for a source of electrical current, said connection means being coupled to said cannula means to provide for electro-cauterization and dissection at said distal end of said cannula means.

5. A surgical device according to claim 4, wherein said cannula means includes mounting means for removably mounting a detachable tool device for performing said electro-cauterization and dissection procedures.

6. A surgical device according to claim 5, wherein said detachable tool device includes a central passageway in substantial alignment with said lumen of said cannula means.

7. A surgical device according to claim 4, wherein said connection means is substantially aligned with a longitudinal axis of said single lumen cannula means.

8. A surgical device according to claim 1, further comprising a sleeve member concentrically positioned about said cannula means and in substantial contact with said cannula means along its length, said sleeve member being longitudinally slidable over said cannula means.

9. A surgical device according to claim 8, wherein said sleeve member is electrically insulated.

10. A surgical device according to claim 9, further comprising connection means for connecting an electrical current to said cannula means for electro-cauterization and dissection at said distal end of said cannula means.

11. A surgical device according to claim 8, wherein said cannula means includes a plurality of apertures positioned adjacent said distal end of said cannula means, said sleeve member being longitudinally slidable to selectively overlay said apertures.

12. A surgical device according to claim 1, wherein said access means comprises a port adapted to accommodate an optical fiber laser means, said access means communicating with said single lumen cannula means through said mixing chamber for transporting said optical fiber laser means to said distal end of said cannula means.

13. A surgical device according to claim 12, wherein said access means is in substantial alignment with a longitudinal axis of said single lumen cannula means, and includes a sealing means to prevent leakage of fluid and suction.

14. A surgical device for hydrodissection of tissue at a surgical site, comprising:
    a handle means including
        first connection means for a source of irrigation fluid, and
        means for actuating said first connection means;
    an endoscopic portion extending from said handle means including
        a single lumen cannula means adapted to communicate with said fluid source through said connection means at a proximal end of said cannula means, said cannula means having a plurality of apertures at a distal end thereof and being positionable adjacent a surgical site to transport said fluid under pressure; and
        a sleeve member concentrically positioned about said cannula means and in substantial contact with said cannula means from said proximal end to said distal end, said sleeve member being longitudinally slidable to overlay at least one of said plurality of apertures in said distal end of said cannula means to vary the pressure of said fluid exiting therefrom.

15. A surgical device according to claim 14, further comprising connection means for an aspirating source and on said handle means for actuating said connection means.

16. A surgical device according to claim 14, further comprising mounting means for mounting a detachable nozzle tip member at a distal end of said cannula means in alignment with a longitudinal axis of said cannula means.

17. A surgical device according to claim 14, further comprising connection means on said handle means for an optical fiber laser means, said connection means being in substantial alignment with a longitudinal axis of said cannula means.

18. A surgical device according to claim 14, further comprising connection means for an electrical current source, said connection means being coupled to said cannula means for electro-cauterization procedures.

19. A surgical device according to claim 18, wherein said sleeve member is electrically insulated.

20. A variably orientable surgical device for irrigating and aspirating a surgical site, said device comprising:
    a handle means including
        first connection means for a source of irrigation fluid
        means for actuating said first connection means
        second connection means for an aspirating source for aspirating said surgical site, and
        means for actuating said second connection means; and
    an endoscopic portion extending from said handle means including
        a single lumen cannula means communicating with said aspirating source and said fluid source through said first and second connection means at a proximal end of said cannula means, said cannula means being positionable adjacent said surgical site at a distal end thereof to selectively transport said fluid and said aspirating force;
    wherein at least one of said connection means is rotatable at least 180° in a plane parallel to said cannula means to positions perpendicular to a longitudinal axis of said cannula means on opposite sides of said longitudinal axis, and said other connection means is positioned at a distal end of said device and substantially parallel to said longitudinal axis of said cannula means.

21. A surgical device according to claim 20, further comprising third connection means in communication with said cannula means for connection to a dissection source for dissecting tissue.

22. A surgical device according to claim 20, further comprising a sleeve member concentrically positioned about said cannula means and in substantial contact therewith, said sleeve member being longitudinally slidable in relation to said cannula means, wherein said cannula means includes a plurality of radially directed apertures at a distal end thereof, said sleeve member being longitudinally slidable to overlay at least one of said plurality of apertures.

23. A surgical device according to claim 20, further comprising connection means in communication with said cannula means for accommodating an optical fiber laser means.

24. A surgical device according to claim 20, further comprising connection means for an electrical current, said connection means coupled to said cannula means for electrocauterization.

25. A surgical device according to claim 24, further comprising mounting means for mounting a dissection tool member at a distal end of said cannula means, said dissection tool being electrically connected to said cannula means for electrocauterization.

26. An endoscopic surgical kit comprising:
    an instrument including
        an elongated body portion having a first end and second end, and
        a handle mechanism at said first end and a coupling mechanism at said second end; and
    a plurality of tool members, each of said tool members being detachably couplable to said coupling mechanism;
    wherein said tool members are selected from the group consisting of scalpels, knives, hydrodissectors, dissectors, blunt dissectors, spatulas, retractors, nozzles and electrocautery dissectors.

27. An endoscopic surgical instrument according to claim 26, wherein said coupling mechanism is positioned on said body portion remote from said handle mechanism.

28. An endoscopic surgical instrument according to claim 26, wherein said tool mechanism includes an operative portion and a coupling portion for coupling with said coupling mechanism.

29. An endoscopic surgical instrument according to claim 26, wherein said body portion includes a central passageway extending along its length from said coupling mechanism and through said handle mechanism.

30. An endoscopic surgical instrument according to claim 29, wherein said tool mechanism includes a central passageway in substantial alignment with said central passageway of said body portion.

31. An endoscopic surgical instrument according to claim 26, wherein said handle mechanism includes means for connecting said handle mechanism to a source of irrigation and a source of suction.

32. An endoscopic surgical instrument according to claim 31, wherein said connection means communicates with a central passageway within said body portion.

* * * * *